United States Patent [19]

Thoene

[11] Patent Number: 5,646,189
[45] Date of Patent: Jul. 8, 1997

[54] PREVENTION OF HIV INFECTION

[76] Inventor: Jess G. Thoene, 1308 Brooks St., Ann Arbor, Mich. 48103

[21] Appl. No.: 492,478

[22] Filed: Jun. 22, 1995

Related U.S. Application Data

[63] Continuation of Ser. No. 136,697, Oct. 15, 1993, abandoned.
[51] Int. Cl.$^6$ ............................................. A16K 31/13
[52] U.S. Cl. ........................................ 514/665; 514/934
[58] Field of Search ................................. 514/665, 934

[56] References Cited

U.S. PATENT DOCUMENTS

| 3,892,824 | 7/1975 | Piper et al. | 260/944 |
| 3,991,190 | 11/1976 | Garzia et al. | 424/251 |
| 5,554,655 | 9/1996 | Thoene | 514/665 |

FOREIGN PATENT DOCUMENTS

| 1 157 774 | 11/1983 | Canada . | |
| 0 174 912 A2 | 9/1985 | European Pat. Off. . | |
| 204989 | 12/1986 | European Pat. Off. . | |
| WO 90/08540 | 8/1990 | WIPO | A61K 31/16 |
| WO 90/14007 | 11/1990 | WIPO . | |
| WO 93/06832 | 4/1993 | WIPO . | |
| WO 94/04185 | 3/1994 | WIPO . | |

OTHER PUBLICATIONS

O. Yamamoto et al, *Chemical Abstracts* 113:55076m, "Low-Dose-Rate Effect of Tritium Beta-Rays on Transfection Activity of Phage DNA Related to an Oxidative Species different from .OH, HO$_2$. O$_2$-. and Hydrogen Peroxide" 1990.
Wainberg, Mark et al, *Chemical Abstracts* 112:48337y, "Inactivation of Human Immunodeficiency Virus Type 1 in Tissue Culture Fluid and in Genital Secretions by the Spermicide Benzalkonium Chloride" 1990.
E.B. Michaels et al, *Chemical Abstracts* 117:258256a, "Pharmaceutical Composition for Inactivating Enveloped Viruses and Sperm" 1992.
Windholtz, "The Merck Index", 10th Edition, Published 1983 by Merck & Co., Inc.—Items 2773, 2775 and 2776.
V.V. Bartsevich et al, *Chemical Abstracts* 113:55075k, "Modifying Effect of Glycerol and Cysteamine on γ-Radiation Induction of λ Prophage in *E. coli* Cells" 1990.
T. Kalebic et al, *Proc. Natl. Acad. Sci. USA*, "Suppression of Human Immunodeficiency Virus Expression in Chronically Infected Monocytic Cells by Glutathione, Glutathione Ester, and N-Acetylcysteine", vol. 88, pp. 986–990, (1991).
R. Djurhuus et al, *Carcinogenesis*, "Modulation of Glutathione Content and the Effecton Methionine Auxotrophy and Cellular Distribution of Homocysteine and Cysteine in Mouse Cell Lines", vol. 12, pp. 241–247, (1991).
R.S. Shulof et al, *Arzneimittal Forschung*, "Treatment of HTLV–III/LAV–Infection Patients with D–Penicillamine", vol. 36, pp. 1531–1534, (1986).
S. Kubota et al, *Aids Research and Human Retroviruses*, "2,3 Dimercapto-1-Propanol Inhibits HIV-1 tat Activity, Viral Production and Infectivity in Vitro", vol. 6, pp. 919–927, (1990).

J.S. Oxford et al, *Chemical Abstracts* 78:119655t, "Inhibitor of the Particle–Associated RNA–Dependent RNA Polymerase of Influenza A and B Viruses" 1973.
*Chemical Abstracts* 85:28782k, "Composition OFR Treatment of Virus Infections" 1976.
J.G. Thoene, *Clinical Research*, "In–Vitro Effectiveness of Aminothols and Disulfides Against HIV–1", vol. 40, p. 246A, Apr. 1992.
J. Cohen, *Science*, "Somber News from the AIDS Front", vol. 260, pp. 1712–1713, (1993).
P.S. Sarin et al, *Chemical Abstracts* 107:108862z, "Inhibition of HTLV–III Replication in Cell Cultures" 1986.
A. Garzia et al, *Chemical Abstracts* 84:155677j, "Composition for Treatment of Virus Infections" 1976.
J. Gainer et al, *Chemical Abstracts* 75:85659t, "Inactivation of the Pseudorabies Virus by Dithiothreitol" 1986.
P.S. Sarin et al, *Nato ASI Ser.*, "Inhibition of HTLV–III Replicationi n Cell Cultures", vol. 120, pp. 329–342 (1986).
*Fields Virology*, 2nd Ed., B.N. Fields, et al, Eds., Raven Press, NY, vol. 1, pp.1075–1089 (1990).
*Fields Virology*, 2nd Ed. B.N. Fields, et al. Eds. Raven Press, NY, vol. 2, pp. 1437–1440, 1452–1477, (1990).
*Fields Virology*, 2nd Ed. B.N. Fields, et al. Eds. Raven Press, NY, vol. 1, pp. 507–548 (1990).
*Fields Virology*, 2nd Ed., B.N. Fields, et al, Eds., Raven Press, NY, vol. 2, pp. 1787–1790 (1990).
*Fields Virology*, 2nd Ed. B.N. Fields, et al. Eds. Raven Press, NY, vol. 2, pp. 1529–1543, (1990).
Dagani, *C&EN*, Nov. 23, 1987, pp. 41–49.
Droge et al, *Am. J. Med.*, vol. 91, pp. 140S–144S, (1991).
Mihm et al, *AIDS*, vol. 5, pp. 497–503 (1991).
Perrin et al, *Pharmac. Ther.*, vol. 12, pp. 255–297 (1981).
Pompei et al, *Experientia*, vol. 33, pp. 1151–1152 (1977).
La Colla et al, *Ann. NY Acad. Sci.*, vol. 284, pp. 294–304 (1977).
La Colla et al, *Experientia*, vol. 31, pp. 797–798 (1975).
Marcialis et al, *Experientia*, vol. 29, pp. 1559–1661 (1973).
Schivo et al, *Experientia*, vol. 32, pp. 911–913 (1976).
Billard et al, *Antimicrobial Agents and Chemotherapy*, vol. 5, pp. 19–24 (1974).
M.S. Marcialis et al, *Experientia*, vol. 30, pp. 1272–1273 (1974).
Staal et al, *The Lancet*, vol. 339, pp. 909–912 (1992).
Roederer et al, *Proc. Natl. Acad. Sci. USA*, vol. 87, pp. 4884–4888, (1990).
Oxford et al, *J. Gen. Virol.*, vol. 18, pp. 11–19 (1973).
Oxford et al, *Ann. NY Acad.*, vol. 284, pp. 613–623 (1977).
Arora et al, *Can. J. Biochem.*, vol. 58, pp. 67–72 (1980).
Pisoni et al, *J. Bio. Chem.*, vol. 260, No. 8, pp. 4791–4798 (1985).
Thoene et al, *J. of Ped.*, vol. 96, No. 6, pp. 1043–1044 (1980).

(List continued on next page.)

*Primary Examiner*—Russell Travers
*Attorney, Agent, or Firm*—Oblon, Spivak, McClelland, Maier & Neustadt

[57] ABSTRACT

Topical application of cysteamine, cystamine, or phosphocysteamine to an appropriate bodily portion of a human is effective for the prevention of HIV infection.

24 Claims, No Drawings

OTHER PUBLICATIONS

Thoene et al, *J. Clin. Invest.*, vol. 58, pp. 180–189 (1976).
Gliniak et al, *J. Bio. Chem.*, vol. 266, No. 34, pp. 22991–22997 (1991).
Leonard et al, *J. Bio. Chem.*, vol. 265, No. 18, pp. 10373–10382 (1990).
Lekutis et al, *J. Acq. Imm. Def. Syn.*, vol. 5, pp. 78–81 (1992).
Papadopulos–Eleopulos et al, *The Lancet*, vol. 338, pp. 1013–1014 (1991).
Cardin et al, *J. Bio. Chem.*, vol. 266, No. 20, pp. 13355–13363 (1991) (Abstract).
Kim et al, *Biochem. Biophys. Res. Comm.*, vol. 179, No. 3, pp. 1614–1619 (1991).
Gahl et al, *New Engl. J. Med.*, vol. 316, pp. 971–977 (1987).
Wilson et al, *J. Am. Chem. Soc.*, vol. 102, pp. 359–363 (1980).
Smolin et al, *Ped. Res.*, vol. 23, No. 6, pp. 616–620 (1988).
Owens et al, *Virology*, vol. 179, pp. 827–833 (1990).
Willey et al, *Proc. Natl. Acad. Sci, USA*, vol. 85, pp. 9580–9584 (1988).
Dedera et al, *J. Vir.*, vol. 65, No. 11, pp. 6129–6136 (1991).
Harakeh et al, *Am. Clin. Nutr.*, vol. 54, pp. 1231S–1235S (1991).
Bacq, *Chemical Protection Against Ionizing Radiation*, IV, "The Protective Compounds", pp. 16–35, Charles C. Thomas, USA.
Thoene, "Orphan Drugs and Orphan Diseases: Clinical Realities and Public Policy", pp. 125–131, Alan R. Liss, Inc., NY 1983.
Thoene, "Cooperative Approaches to Research and Development of Orphan Drugs", pp. 157–162, Alan R. Liss, Inc., 1985.
Turner, *Med. J. Austral.*, vol. 153, p. 502 (1990).
Bergamini et al, *J. Clin. Invest.*, vol. 93, pp. 2251–2257 (1994).
Ryser et al, *Proc. Natl. Acad. Sci. USA*, vol. 91, pp. 4559–4563 (1994).
Schroeder et al, CA 110: 1815e 1989.
Hotz et al, CA 81: 101420q 1974.
CA 78: 119655t 1973.
CA 85: 28782k 1976.
CA 113: 55076m 1990.
CA 112: 48337y 1990.
CA 117: 258256a 1992.
Windholtz, "The Merck Index", 10th edition, published 1983 by Merck & Co., Inc. items 2773, 2775 and 2776 1983.
CA 113: 55075k 1990.
Oxford 78CA: 119655t, 1973.
Bartsevich et al. 113CA: 55075k, 1990.
Wainburg et al. 112CA: 48337y, 1990.
Merk Index 10th Ed #2771 & 2776.
Istituto Chemioterapico Italiano, CA 85: 28728k, 1976.

PREVENTION OF HIV INFECTION

This application is a Continuation of application Ser. No. 08/136,697, filed on Oct. 15, 1993, now abandoned.

BACKGROUND OF THE INVENTION

1. Field of the Invention

The present invention relates to methods, compositions, and articles, effective for the prevention of HIV infection.

2. Discussion of the Background

Acquired immunodeficiency syndrome (AIDS) and AIDS related complex (ARC) are caused by infection with human immunodeficiency virus (HIV). Infection with HIV leads to AIDS in over 90% of infected individuals within a ten-year period. There is already a large number of individuals infected with HIV. Accordingly, the number of patients suffering from AIDS will continue to increase for the foreseeable future.

AZT (zidovudine) has received FDA approval for the treatment of AIDS and ARC. However, AZT can cause severe side effects, such as anemia. In addition, there are strains of HIV-1 which are resistant to treatment with AZT.

Cysteamine (2-aminoethanethiol) shows good in vitro activity against HIV. When added twice-daily to cultures of CEM-T$_4$ lymphocytes, cysteamine at 100 µM shows excellent protection against HTLVIII$_B$ with treated cells showing 133% of control survival, and no toxicity (120.8% of control) (Thoene, J., *Clin. Res. Abstract*, May, 1992)). Experiments on other cell lines and with other HIV strains substantiate the antiviral effect of cysteamine against HIV, and its lack of cellular toxicity at concentrations which completely inhibit the virus. Cystamine, the disulfide of cysteamine, also demonstrates substantial activity against the HIV pathogen, and shows little cytotoxicity at 100 µM concentration.

Preventing sexual transmission of the AIDS pathogen is at least as important to the public health as is finding a cure for AIDS. Recent reports which raise doubts about the efficacy of AZT have reinforced the need for agents which reduce or prevent person-to-person spread of HIV. This finding was emphasized in a review of the Berlin IX International AIDS conference, in which Michael Merson, head of the World Health Organization's Global Program on AIDS, was reported to have " . . . implored scientists to develop a vaginal microbicide that could defeat HIV and other pathogens . . . " (Cohen, Jon, *Science*, vol. 260, 1712–1713 (1993)).

Thus, although a number of antiviral agents have been identified for the treatment of AIDS, to date, no effective agents for the prophylaxis of HIV infection are available. Thus, there remains a need for methods and compositions which are effective for the prevention of HIV infection.

SUMMARY OF THE INVENTION

Accordingly, it is one object of the present invention to provide novel methods for the prevention of HIV infection.

It is another object of the present invention to provide novel compositions useful for the prevention of HIV infection.

It is another object of the present invention to provide novel articles useful for the prevention of HIV infection.

These and other objects, which will become apparent during the following detailed description, have been achieved by the inventor's discovery that cysteamine, cystamine, and phosphocysteamine may be used to arrest the sexual transmission of HIV when incorporated into, e.g., vaginal suppositories, condom lubricants, vaginal foams, and other barrier-enhancing methods of sexually transmitted disease control.

DETAILED DESCRIPTION OF THE PREFERRED EMBODIMENTS

Thus, in a first embodiment, the present invention relates to a method for preventing HIV infection by the topical application of an effective amount of cysteamine, cystamine, phosphocysteamine, or a pharmaceutically acceptable salt hereof. Cysteamine is a known compound of the formula

Cysteamine may be prepared from ethanolamine and carbon disulfide via 2-mercaptothiazoline (Gabriel et al, *Ber.*, vol. 31, 2837 (1898); Knorr et al, *Ber.*, vol. 36, 1281 (1903); and Mills, Jr. et al, *J. Am. Chem. Soc.*, vol. 62, 1173 (1940)) or via ethyleneimine (Wenker, *J. Am. Chem. Soc.*, vol. 57, 2328 (1935); Mills, Jr. et al, *J. Am. Chem. Soc.*, vol. 62, 1173 (1940); and Shirley, *Preparation of Organic Intermediates*, Wiley, NY p. 189 (1951)).

Cysteamine is useful for the treatment of nephropathic cystinosis (Thoene et al, *The Journal of Clinical Investigation*, vol. 58, pp. 180–189 (1976); Thoene et al, *The Journal of Pediatrics*, vol. 96, pp. 1043–1044 (1980); Thoene, in *Orphans Drugs and Orphan Diseases: Clinical Realities and public Policy*, Alan R. Liss, NY, pp. 125–131 (1983); Thoene, in *Cooperative Approaches to Research and Development of Orphan Drugs*, Alan R. Liss, NY pp. 157–162 (1985); Pisoni et al, *The Journal of Biological Chemistry*, vol. 260, pp. 4791–4798 (1985); Gahl et al, *New England Journal of Medicine*, vol. 316, pp. 971–977 (1987); and Smolin et al, *Pediatric Research*, vol. 23, pp. 616–620 (1988).

Cystamine has the formula

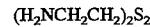

and may be prepared by the H$_2$O$_2$ oxidation of cysteamine (Mills, Jr. et al, *J. Am. Chem. Soc.*, vol. 62, 1173 (1940); and Barnett, *J. Chem. Soc.*, 1944, 5).

Phosphocysteamine is the phosphorothioester of cysteamine and has the formula

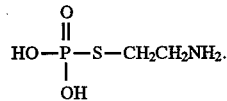

Phosphocysteamine is also known to be useful for the treatment of nephropathic cystinosis (Thoene et al, *The Journal of Pediatrics*, vol. 96, pp. 1043–1044 (1980); Thoene, in *Cooperative Approaches to Research and Development of Orphan Drugs*, Alan R. Liss, NY, pp. 157–162 (1985); and Smolin et al, *Pediatric Research*, vol. 23, pp. 616–620 (1988)).

Cysteamine is known to be safe for use in humans and does not give rise to any frequent side-effects serious enough to require discontinuation of the drug. There is both in vitro and in vivo data about the safety of cysteamine when applied topically. Studies on the effect of cysteamine on the growth rate and cloning efficiency of epithelial fibroblasts show no effect on growth rate at concentrations up to 10 µM, but severe loss in cloning efficiency at that concentration. One hundred μM cysteamine caused an apparent two-fold increase in the doubling time and reduced the cloning efficiency to zero (Thoene, J., et al, R., *J. Clin. Invest*, vol. 58, pp. 180–189 (1976)). These in vitro experiments were performed using fibroblasts which are not protected as are cornified epithelial cells, in vivo, as found in the oral, vaginal and anal cavities.

More appropriate are the studies of topical cysteamine for use in the treatment of the keratitis of cystinosis. In this formulation, aqueous cysteamine at concentrations of 0.1% and 0.5%, which correspond to 10 mM and 50 mM, respectively, were used. These concentrations are effective in reducing the cystine crystals found in the corneas of patients with nephropathic cystinosis, and the drug is well-tolerated in chronic use via this modality. Rabbit studies have shown both concentrations to be safe as evaluated via the Draize test (Kaiser-Kupfer, M. et al, *Archives of Ophthalmology*, vol. 108, pp. 689–693 (1990); and Kaiser-Kupfer, M. et al, *New Eng. J. Med.*, vol. 316, pp. 775–779 (1987)).

Preferably, the present method involves the topical application of cysteamine or a pharmaceutically acceptable salt thereof.

In the context of the present invention, it is to be understood that the term topical application includes application to the body cavities as well as to the skin. Thus, in a preferred embodiment, cysteamine, cystamine, phosphocysteamine or pharmaceutically acceptable salt thereof is applied to a body cavity such as the anus, the mouth, or the vagina. In a particularly preferred embodiment, cysteamine or a pharmaceutically acceptable salt thereof is applied to the vagina.

Thus, the present method may involve topical application to the vagina to prevent HIV infection as a result of vaginal intercourse. Typically, the topical application is carried out prior to the beginning of vaginal intercourse, suitably 0 to 60 minutes, preferably 0 to 5 minutes, prior to the beginning of vaginal intercourse. Suitably cysteamine is applied in an amount that will result in a local concentration of 0.025 mM to 1M, preferably 0.5 mM to 500 mM, most preferably 25 mM to 50 mM, throughout the vagina. In the case of cystamine, the suitable, preferred, and most preferred dosages correspond to the same respective dosages of cysteamine in terms of weight and one half those of cysteamine in terms of moles. In the case of phosphocysteamine, the suitable, preferred, and most preferred dosages are the same as those of cysteamine in terms of moles.

The cysteamine may be applied to the vagina in a number of forms including aerosols, foams, jellies, creams, suppositories, tablets, tampons, etc. Spermicidal compositions suitable for application to the vagina are disclosed in U.S. Pat. Nos. 2,149,240, 2,330,846, 2,436,184, 2,467,884, 2,541,103, 2,623,839, 2,623,841, 3,062,715, 3,067,743, 3,108,043, 3,174,900, 3,244,589, 4,093,730, 4,187,286, 4,283,325, 4,321,277, 4,368,186, 4,371,518, 4,389,330, 4,415,585, and 4,551,148, which are incorporated herein by reference, and the present method may be carried out by applying cysteamine, cystamine, phosphocysteamine or a pharmaceutically acceptable salt thereof to the vagina in the form of such a composition.

It should be noted that it is not necessary that a spermicidal active agent other than cysteamine, cystamine, phosphocysteamine or pharmaceutically acceptable salt thereof be present in the composition. Rather, in some embodiments, it may be suitable that no additional spermicidal agent be present in the composition. Thus, at intravaginal concentrations higher than about 100 mM, cysteamine itself will effectively lyse the sperm. The higher concentrations provide a superior anti-HIV effect by both inactivating virus present extracellularly, and by killing cells in which it resides, producing cell lysis and thus exposing those virions within to destruction by the microbicides.

Further, when only the female is infected with HIV, it is not necessary that the sperm be killed in order to prevent the sexual transmission of the disease.

The composition containing the cysteamine, cystamine, phosphocysteamine or pharmaceutically acceptable salt thereof may be applied to the vagina in any conventional manner. Suitable devices for applying the composition to the vagina are disclosed in U.S. Pat. Nos. 3,826,828, 4,108,309, 4,360,013, and 4,589,880, which are incorporated herein by reference.

In another embodiment, the present invention involves topical administration of cysteamine, cystamine, phosphocysteamine or a pharmaceutically acceptable salt thereof to the anus. Suitably, the cysteamine, cystamine, phosphocysteamine or pharmaceutically acceptable salt is applied in an amount which results in a local anal concentration of 0.025 mM to 1M, preferably 0.5 mM to 500 mM, most preferably 25 mM to 50 mM. The composition administered to the anus is suitably a foam, cream, jelly, etc., such as those described above with regard to vaginal application. In the case of anal application, it may be preferred to use an applicator which distributes the composition substantially evenly throughout the anus. For example, a suitable applicator is a tube 2.5 to 25 cm, preferably 5 to 10 cm, in length having holes distributed regularly along its length.

In another embodiment, the present method may be carried out by applying cysteamine, cystamine, phosphocysteamine, or a pharmaceutically acceptable salt orally. Oral application is suitably carried out by applying a composition which is in the form of a mouthwash or gargle. Oral application is especially preferred to prevent infection during dental procedures. Suitably, the composition is applied just prior to the beginning of the dental procedure and periodically throughout the procedure. In this embodiment, the cysteamine, cystamine, phosphocystamine, or pharmaceutically acceptable salt thereof is present in the mouthwash or gargle in a concentration of 0.025 mM to 1M, preferably 0.5 mM to 500 mM, most preferably 25 mM to 50 mM.

The present method also includes administration of mixtures of cysteamine, cystamine, phosphocysteamine or salts thereof. For purposes of the present invention, the term pharmaceutically acceptable salt thereof refers to any salt of cysteamine, cystamine, or phosphocysteamine which is pharmaceutically acceptable and does not greatly reduce or inhibit the anti-HIV activity of cysteamine, cystamine, or phosphocysteamine. Suitable examples include acid addition salts, with an organic or inorganic acid such as acetate, tartrate, trifluoroacetate, lactate, maleate, fumarate, citrate, methanesulfonate, sulfate, phosphate, nitrate, or chloride. The use of trifluoroacetate, nitrate, or methane-sulfonate salts in vaginal or anal compositions may not be preferred due to irritation. In addition, for phosphocysteamine either or both of the hydrogen atoms on the phosphoryl group may be replaced with any suitable cation, such as $Na^+$, $K^+$, $Mg^{+2}$, $Ca^{++}$, $NH_4^+$, $NR_4^+$ (where R is a $C_{1-4}$ alkyl).

It is to be further understood that the terms cysteamine, cystamine, phosphocysteamine, and pharmaceutically acceptable salts thereof include all the hydrated forms of these compounds as well as the anhydrous forms.

The present invention also provides compositions useful for preventing the spread of HIV infection. As noted above, such compositions may be in the form of foams, creams, jellies, suppositories, tablets, aerosols, gargles, mouthwashes, etc. Particularly preferred are vaginal suppositories. The concentration of cysteamine, cystamine, phosphocysteamine or pharmaceutically acceptable salt in the composition is such to achieve the local vaginal, anal, or oral concentrations described above upon administration of the usual amount of the type of composition being applied.

In this regard, it is noted that when the composition is in the form of a suppository (including vaginal suppositories), the suppository will usually be 1 to 5 grams, preferably about 3 grams, and the entire suppository will be applied. A vaginal tablet will suitably be 1 to 5 grams, preferably about 2 grams, and the entire tablet will be applied. When the composition is vaginal cream, suitably 0.1 to 2 grams, preferably about 0.5 grams of the cream will be applied. When the composition is a water-soluble vaginal cream, suitably 0.1 to 2 grams, preferably about 0.6 grams, are applied. When the composition is a vaginal spray-foam, suitably 0.1 to 2 grams, preferably about 0.5 grams, of the spray-foam are applied. When the composition is a vaginal soluble waffle, suitably the waffle is 0.1 to 2 grams, preferably about 0.3 grams, and the entire waffle is applied. When the composition is an anal cream, suitably 0.1 to 2 grams, preferably about 0.5 grams of the cream is applied. When the composition is an anal spray-foam, suitably 0.1 to 2 grams, preferably about 0.5 grams of the spray-foam are applied. When the composition is a mouthwash or gargle, suitably 1 to 10 ml, preferably about 5 ml are applied.

In some applications, it may be preferred that the composition also contain a spermicide. Examples of suitable spermicides are disclosed in the U.S. patents cited and incorporated herein by reference above. Preferred spermicides include nonylphenoxypolyoxyethylene glycol (nonoxynol 9), benzethonium chloride, and chlorindanol. Suitably, the pH of the composition is 4.5 to 8.5. Vaginal compositions preferably have a pH of 4.5 to 6, most preferably about 5. In the case of phosphocysteamine, the pH is preferably above 7.

In the case of a mouthwash or gargle, it may be preferred to include in the composition an agent which will mask the taste and/or odor of the cysteamine, cystamine, and/or phosphocysteamine. Such agents include those flavoring agents typically found in mouthwashes and gargles, such as spearmint oil, cinnamon oil, etc.

The present compositions may also be in the form of a time-release composition. In this embodiment, cysteamine, cystamine, and/or phosphocysteamine is incorporated in a composition which will release cysteamine, cystamine and/ or phosphocysteamine at a rate which will result in the vaginal or anal concentration described above. Time-release compositions are disclosed in *Controlled Release of Pesticides and Pharmaceuticals*, D. H. Lew, Ed., Plenum Press, New York, 1981; and U.S. Pat. Nos. 5,185,155; 5,248,700; 4,011,312; 3,887,699; 5,143,731; 3,640,741; 4,895,724; 4,795,642; Bodmeier et al, *Journal of Pharmaceutical Sciences*, vol. 78 (1989); Amies, *Journal of Pathology and Bacteriology*, vol. 77 (1959); and Pfister et al, *Journal of Controlled Release*, vol. 3, pp. 229–233 (1986), all of which are incorporated herein by reference. It should also be understood that when the time-release composition contains either cystamine or phosphocysteamine, it may be desirable to include in the time-release composition an agent which is capable of converting cystamine or phosphocysteamine into cysteamine. In the case of cystamine, the agent may be any reducing agent capable of converting cystamine to cysteamine, such as glutathione. In the case of phosphocysteamine, the agent could be any phosphatase capable of converting phosphocysteamine to cysteamine and which retains its activity in the local environment (vagina, anus, mouth, etc.), such as bovine or human prostatic acid phosphatase or alkaline phosphatase. In vaginal applications, the use of prostatic acid phosphatase is preferred.

The present compositions may also be in the form which releases cysteamine, cystamine, and/or phosphocysteamine in response to some event such as vaginal or anal intercourse. For example, the composition may contain cysteamine, cystamine, and/or phosphocysteamine in vesicles or liposomes which are disrupted by the mechanical action of intercourse. Compositions comprising liposomes are described in U.S. Pat. No. 5,231,112 and Deamer and Uster, "Liposome Preparation: Methods and Mechanisms", in *Liposomes*, pp. 27–51 (1983); Sessa et al, *J. Biol. Chem.*, vol. 245, pp. 3295–3300 (1970); *Journal of Pharmaceutics and Pharmacology*, vol. 34, pp. 473–474 (1982); and *Topics in Pharmaceutical Sciences*, D. D. Breimer and P. Speiser, Eds., Elsevier, New York, pp. 345–358 (1985), which are incorporated herein by reference. Again, in the case of cystamine and phosphocysteamine, it may be desirable to include in the composition an agent which will convert the released cystamine and/or phosphocysteamine to cysteamine.

It should also be realized that the present compositions may be associated with an article, such as an intrauterine device (IUD), vaginal diaphragm, vaginal sponge, pessary condom, etc. In the case of an IUD or diaphragm, time-release and/or mechanical-release compositions may be preferred, while in the case of condoms, mechanical-release compositions are preferred.

In another embodiment, the present invention provides novel articles which are useful for the prevention of HIV infection. In particular, the present articles are those which release cysteamine, cystamine, and/or phosphocysteamine when placed on an appropriate body part or in an appropriate body cavity. As in the case of the above-described compositions, it may be preferred that the present articles also release an agent capable of converting cystamine or phosphocysteamine into cysteamine. Thus, the present invention provides IUDs, vaginal diaphragms, vaginal sponges, pessaries, or condoms which contain or are associated with cysteamine, cystamine, and/or phosphocysteamine or a composition containing cysteamine, cystamine and/or phosphocysteamine.

Thus, the present article may be an IUD which contains cysteamine, cystamine, and/or phosphocysteamine. Suitable IUDs are disclosed in U.S. Pat. Nos. 3,888,975 and 4,283, 325 which are incorporated herein by reference.

The present article may be an intravaginal sponge which comprises and releases, in a time-controlled fashion, cysteamine, cystamine, and/or phosphocysteamine. Intravaginal sponges are disclosed in U.S. Pat. Nos. 3,916,898 and 4,360,013, which are incorporated herein by reference. The present article may also be a vaginal dispenser which releases cysteamine, cystamine, and/or phosphocysteamine. Vaginal dispensers are disclosed in U.S. Pat. No. 4,961,931, which is incorporated herein by reference.

The present article may also be a condom which is coated with cysteamine, cystamine, and/or phosphocysteamine. In a preferred embodiment, the condom is coated with a lubricant or penetration enhancing agent which comprises cysteamine, cystamine, and/or phosphocysteamine. In a particularly preferred embodiment, the lubricant or penetration enhancing agent comprises cysteamine, cystamine, and/ or phosphocysteamine which is encapsulated in liposomes such that the cysteamine, cystamine and/or phosphocysteamine is released from the liposomes upon intercourse. Lubricants and penetration enhancing agents are described in U.S. Pat. Nos. 4,537,776; 4,552,872; 4,557,934; 4,130, 667, 3,989,816; 4,017,641; 4,954,487; 5,208,031; and 4,499,154, which are incorporated herein by reference. In another preferred embodiment, cysteamine, cystamine, and/or phosphocysteamine is contained inside the condom. In a particularly preferred embodiment, cysteamine, cystamine, and/or phosphocysteamine is contained in a reservoir in the tip of the condom.

Although not intended to be limiting in any way, a possible explanation of the efficacy of cysteamine for the treatment of HIV infections is as follows. Human immunodeficiency virus contains two coat proteins (GP120 and GP41). GP120 is a transmembrane protein which forms a domain on the exterior surface of the virus which recognizes the CD4 receptor on a subpopulation of T lymphocytes. It is thought that the recognition between the GP120 coat protein and the CD4 receptor not only leads to infection of cells by the virus but also mediates cell death by promoting autofusion, syncytia formation, and other toxic effects not yet well characterized. Crucial to the above reaction is the presence of disulfide bonds which maintain the tertiary structure of the exterior portion of GP120. It is these intrachain disulfide bonds that may be the target for cysteamine. Cysteamine is known to be highly effective in promoting intrachain disulfide scission by direct reaction with the disulfides, leading to mixed disulfides at each end of the pre-existing cystine resides. Such a reaction may lead to disruption of the tertiary structure of the GP120 molecule, altering its configuration, and inhibit binding to the CD4 receptor, inhibiting viral entry, autofusion, and other toxic effects of HIV.

Other features of the invention will become apparent in the course of the following descriptions of exemplary embodiments which are given for illustration of the invention and are not intended to be limiting thereof.

EXAMPLES

I. Some examples are herebelow given relating to compositions according to the invention, which contain cysteamine.

| Vaginal suppositories | |
|---|---|
| Composition for a 3-gram suppository: | |
| Cysteamine | 0.005 g |
| Hexantriol | 0.1 g |
| Polyglycol 1500 balance to | 3 |

| Vaginal tablets | |
|---|---|
| Composition for a 2-gram tablet: | |
| Cysteamine | 0.004 g |
| Anhydrous citric acid | 0.7 g |
| Sodium bicarbonate | 0.3 g |
| Polyglycol 6000 | 0.4 g |
| Lactose balance to | 2 g |

| Vaginal Cream | |
|---|---|
| Percentage composition: | |
| Cysteamine | 1 g |
| Nonionic autoemulsifying base | 4 g |
| Water balance to | 100 g | for each application 0.5 grams of the cream are vaginally administered with a suitable syringe.

| Water-soluble vaginal cream | |
|---|---|
| Percentage compositions: | |
| Cysteamine | 1 g |
| Polyglycol 400 | 30 g |
| Polyglycol 6000 | 8.5 g |
| Hexantriol | 3 g |
| Water balance to | 100 g |

For each application, 0.6 grams of the cream are vaginally administered with a suitable syringe.

| Vaginal spray-foam | |
|---|---|
| Percentage composition: | |
| Cysteamine | 1 g |
| Polyglycol 6000 | 2 g |
| Nonionic emulsifying agent | 2 g |
| Water | 85 g |
| Freon 12/144 (70.30) | 10 g |

For each application 0.5 grams of the foam are vaginally administered.

| Vaginal soluble waffle | |
|---|---|
| Composition for one 0.340-gram waffle: | |
| Cysteamine | 0.003 g |
| Starch | 0.040 g |
| Water-soluble lanolin | balance to 0.340 g |

II. Additional examples are prepared as follows.

Vaginal Suppository

| A. | Components | Percent by weight |
|---|---|---|
| | polyethylene glycol 1000 | 65.0 |
| | polyethylene glycol 300 NF | 3.0 |
| | cellulose | 1.0 |
| | alginic acid (80 mesh) | 15.0 |
| | sodium bicarbonate (100 mesh) | 12.0 |
| | Cysteamine | 4.0 |

This composition is prepared as follows. The two polyethylene glycols are melted together at a temperature of about 62°–68° C. When the melt is complete, the cysteamine is added to the melt under an atmosphere of $N_2$ with agitation, the agitation being continued for sufficient time to totally mix the ingredients, usually from about 5 to 10 minutes. The cellulose is then dispersed into the mixture under slow-speed agitation, after which first the sodium bicarbonate and then the alginic acid is added. Agitation is continued for about 15 to 30 minutes to completely disperse the latter ingredients into the mixture. During this period, the temperature is maintained substantially constant. Thereafter, the mass is cooled to about 52° C. and is then poured in torpedo-shaped molds which have been pre-chilled to about 15°–20° C. The molds are then placed in freezing cabinets until the mass is thoroughly chilled. The products are thereafter removed from the molds, ready for use or storage.

| B. | Components | Percent by weight |
|---|---|---|
| | polyethylene glycol 1000 | 53.0 |
| | polyethylene glycol 300 | 11.7 |
| | cellulose | 1.0 |
| | methyl cellulose | 1.0 |
| | alginic acid | 16.7 |
| | sodium bicarbonate | 13.3 |
| | Cysteamine | 3.3 |

The above ingredients are mixed together in the manner described in Example IIA and treated at the temperature and for the periods described in Example IIA.

III. An additional example of a vaginal gel is prepared as follows.

Vaginal Gel

| | Percent by wt/vol. |
|---|---|
| Cysteamine | 1 |
| Poloxamer-407-(Pluronic F-127) (MW 11,500) | 18 |
| PEG 400 | 20 |
| Glycerin | 20 |
| Polysorbate 60 | 3 |
| BHA | .02 |
| Water qs ad | 100 |

The composition is prepared by mixing all the ingredients under an atmosphere of $N_2$ with approximately 90% of the required water and allowing the polyoxyethylenepolyoxypropylene block copolymer to hydrate and completely dissolve with gentle stirring. When a clear gel is obtained, the remaining water is added to adjust the volume to 100 ml.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A method of inhibiting transmission of HIV infection, comprising topically applying an effective amount of a compound selected from the group consisting of cysteamine, cystamine, phosphocysteamine, and pharmaceutically acceptable salts thereof.

2. The method of claim 1, wherein said compound is topically applied to a subject's vagina.

3. The method of claim 1, wherein said compound is topically applied to a subject's anus.

4. The method of claim 1, wherein said compound is topically applied to a subject's oral cavity.

5. The method of claim 1, comprising coapplication of a spermicide.

6. The method of claim 1, wherein said compound is cysteamine.

7. The method of claim 2, wherein said compound is cysteamine.

8. The method of claim 3, wherein said compound is cysteamine.

9. The method of claim 4, wherein said compound is cysteamine.

10. The method of claim 5, wherein said compound is cysteamine.

11. The method of claim 1, wherein said compound is cystamine.

12. The method of claim 2, wherein said compound is cystamine.

13. The method of claim 3, wherein said compound is cystamine.

14. The method of claim 4, wherein said compound is cystamine.

15. The method of claim 5, wherein said compound is cystamine.

16. The method of claim 1, wherein said compound is phosphocysteamine.

17. The method of claim 2, wherein said compound is phosphocysteamine.

18. The method of claim 3, wherein said compound is phosphocysteamine.

19. The method of claim 4, wherein said compound is phosphocysteamine.

20. The method of claim 5, wherein said compound is phosphocysteamine.

21. The method of claim 1, wherein said compound is comprised in a composition in the form of a foam, jelly, cream, tablet, suppository, aerosol, gargle, or mouthwash.

22. The method of claim 1, which is in the form of a vaginal suppository.

23. The method of claim 1, wherein said compound is cysteamine and is topically applied to a subject's vagina, anus, or oral cavity in an amount sufficient to result in a local concentration of cysteamine of 0.025 mM to 1M in said vagina, anus, or oral cavity.

24. The method of claim 1, wherein said compound is cysteamine and is topically applied in an amount sufficient to result in a local concentration of cysteamine of 0.5 mM to 500 mM in said vagina, anus, or oral cavity.

* * * * *